United States Patent
Pasricha et al.

(10) Patent No.: US 8,211,941 B2
(45) Date of Patent: Jul. 3, 2012

(54) ANTAGONISTS OF THE TRANSIENT RECEPTOR POTENTIAL VANILLOID 1 AND USES THEREOF

(75) Inventors: Pankaj J. Pasricha, Cupertino, CA (US); Jiande Chen, Houston, TX (US); Rami Hawari, Hampton Cove, AL (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/082,598

(22) Filed: Apr. 11, 2008

(65) Prior Publication Data
US 2009/0012154 A1   Jan. 8, 2009

Related U.S. Application Data

(60) Provisional application No. 60/923,112, filed on Apr. 12, 2007.

(51) Int. Cl.
*A61K 31/216* (2006.01)
(52) U.S. Cl. .................................................. 514/511
(58) Field of Classification Search .................. None
See application file for complete search history.

(56) References Cited

U.S. PATENT DOCUMENTS 5,846,235 A * 12/1998 Pasricha et al. ............. 606/23

OTHER PUBLICATIONS

Horn et al., Autonomic Neuroscience, 115(1-2), (Sep. 30, 2004), 74-81.*
Linscheer et al., Gastroenterology, (Oct. 1979) (4 Pt.1): 642-6 (Abstract).*
Yamakuni, et al. *Resinferatoxin Antagonizes Cisplatin-Induced Emesis in Dogs and Ferrets;* European Journal of Pharmacology, 2002, vol. 442, No. 3, pp. 273-278.
Andrews, et al. *Resinferatoxin, an Ultrapotent Capsaicin Analogue, Has Anti-Emetic Properties in the Ferret;* Neuropharmacology, 1993, vol. 32, No. 8, pp. 799-806.
Cheng, et al. *Evaluation of the Anti-Emetic Potential of Anti-Migraine Drugs to Prevent Resiniferatoxin-Induced Emesis in Suncus Murinus (House Musk Shrew);* European Journal of Pharmacology, 2005, vol. 508, pp. 231-238.
Andrews, et al. *The Emetic and Anti-emetic Effects of the Capsaicin Analogue Resiniferatoxin in Suncus Murinus, the House Musk Shrew;* British Journal of Pharmacology, 2000, vol. 106, No. 6, pp. 1247-1254.

* cited by examiner

*Primary Examiner* — Phyllis G. Spivack
(74) *Attorney, Agent, or Firm* — Landrum Intellectual Property

(57) ABSTRACT

One of the major disabling symptoms of gastroparesis is nausea and vomiting which can be difficult to control with currently available treatments. It is postulated that signaling of gastrointestinal causes of nausea starts with activation of vagal afferent nerves that trigger the central emetic pathway. Most vagal afferent nerves are unmyelinated C-fibers, many of which express the vanilloid receptor TRPV1 and respond to capsaicin. Resiniferatoxin is a very potent capsaicin analogue that has a much more favorable ratio of desensitization to excitation than capsaicin leading to more effective desensitization without irritation. The present invention describes methods of alleviating acute or chronic nausea, vomiting by the administration of resiniferatoxin.

3 Claims, 1 Drawing Sheet

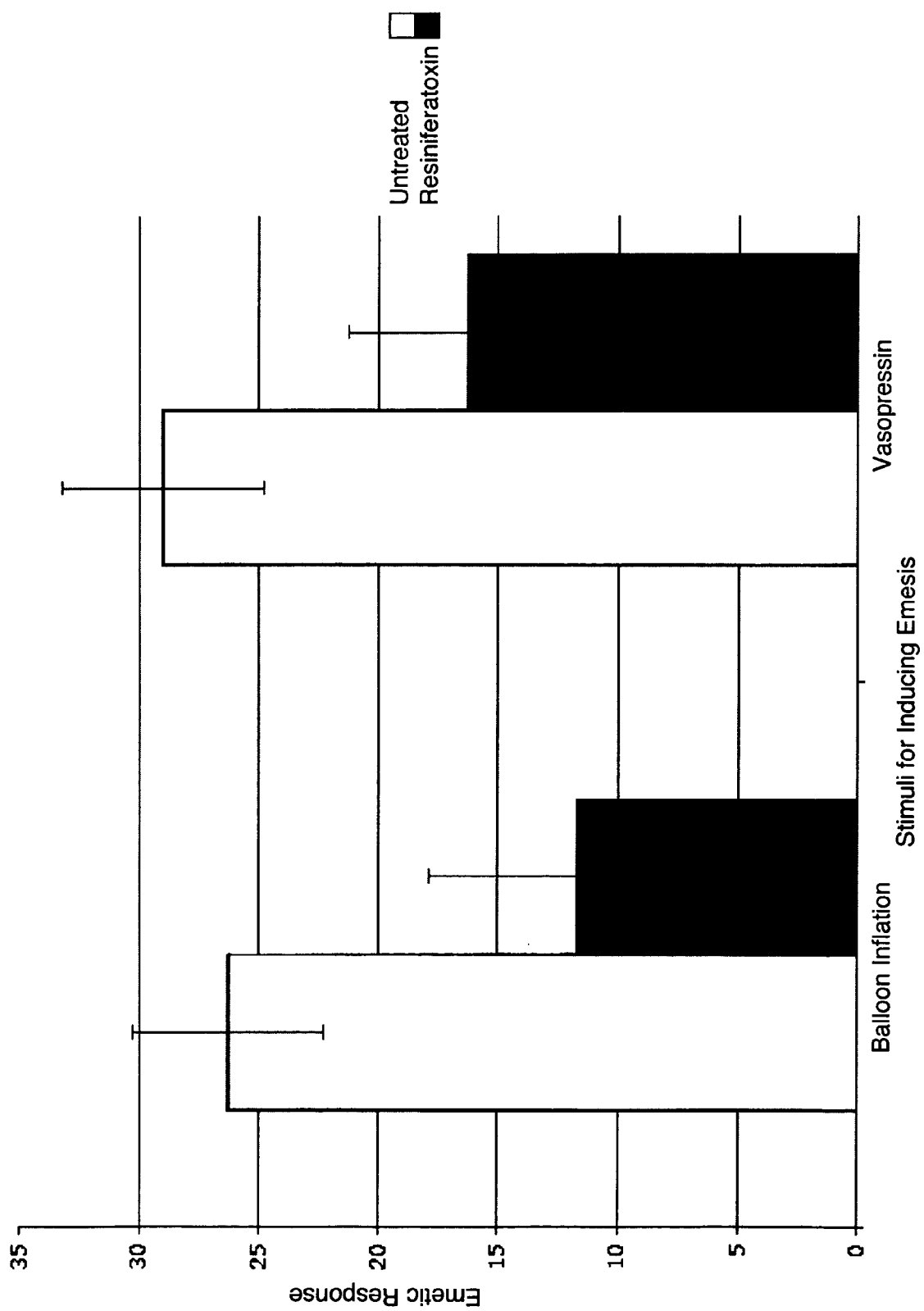

ANTAGONISTS OF THE TRANSIENT RECEPTOR POTENTIAL VANILLOID 1 AND USES THEREOF

CROSS-REFERENCE TO RELATED APPLICATION

This non-provisional application claims benefit of priority of provisional application U.S. Ser. No. 60/923,112, filed Apr. 12, 2007, now abandoned.

BACKGROUND OF THE INVENTION

1. Field of the Invention

The present invention relates to the field of gastrointestinal disorders. More specifically, the present invention discloses a method used for the treatment of acute or chronic nausea, vomiting or combination thereof in an individual by administering resiniferatoxin or derivatives.

2. Description of the Related Art

Vomiting or emesis is the expulsion of gastrointestinal contents through the mouth brought about by the descent of the diaphragm, forceful contractions of the abdominal muscles and chest wall muscles and relaxation of gastric cardia. Nausea is the behavioral and emotional state that usually leads to the unpleasant need to vomit. Nausea usually precedes and follows vomiting but it could sometimes be isolated or occur only after vomiting started. Nausea and vomiting are usually labeled acute if the symptoms were present for less than one week. Chronic symptoms usually last for more than one week.

The nausea/vomiting reflex is triggered by either peripheral or central stimuli. The peripheral stimuli activate the chemoreceptor and/or mechanoreceptors in the gastrointestinal wall. Physical damage as in inflammation and tissue injury, distension as in bowel obstruction or abnormal gastrointestinal motility as in gastroparesis activates mechanoreceptors. Toxins and culprit food contents are responsible for activating the chemoreceptor. The signal from these stimuli is carried by the afferent nerve fibers in the sensory Vagus and abdominal splanchnic nerves. These nerve fibers converge onto the vomiting center and the sensory vagus nucleus: the nucleus tractus solitaris. The vomiting center in the medulla of the brain stem is not a specific anatomical area but rather a neuronal network interconnection.

In addition to the peripheral Vagal afferents, central neuronal nerve afferent converge from the inner ear e.g. motion sickness, cranial pressure receptors e.g. meningitis, cerebral cortex e.g. psychogenic nausea and vomiting and the chemoreceptor trigger zone (CTZ). The chemoreceptor trigger zone is located in the area postrema of the fourth ventricle outside the blood brain barrier allowing it to function as a sensor for blood borne emetic stimuli including for example drugs and toxins and inflammatory mediators released during some illness. The motor Vagus nerve, other cranial nerves and the sympathetic pathway carry the efferent signal from the vomiting center. The end effect is stimulation of the salivary gland, pharyngeal, gastrointestinal and respiratory muscles to result in the coordinated event that is vomiting. Efferent nerves to the cerebral cortex and limbic system are thought to be responsible for the perception of nausea.

Chemotherapeutic and radiation induced nausea and vomiting is classically described as anticipatory, acute or delayed. Anticipatory nausea and vomiting is mediated through the central pathway as in psychogenic emesis. Acute and delayed emesis is separated by twenty-four hour cutoff. Based on the knowledge of some the neurotransmitters involved in these pathways, different pharmaceutical targets have been used to treat nausea and vomiting. This includes blocking the dopamine type-2 receptors in the chemoreceptor trigger zone and nucleus tractus solitares with agents such as prochlorperazine and metoclopramide. 5-HydroxyTryptamine subtype 3 receptors (5HT-3) are present in the chemoreceptor trigger zone and the gastrointestinal tract and it is thought that 5-HT released from the enterochromaffin cells in the gastrointestinal tract acts on 5-HT-3 receptors to initiate the vomiting reflex. Ondansetron is an example of a 5HT-3 blocker. Neurokinin-1 (NK-1) receptor blocker aprepitant inhibits the action of substance P, the ligand for NK-1 receptor. It is postulated that the nucleus tractus solitaris and the vomiting center contain NK-1 receptors and that substance P is a strong emetic. Other neurotransmitters involved in the vomiting neuro-pathway are opioids, histamine and cholinergic receptors.

Resiniferatoxin (RTX) is a naturally occurring super-analogue of capsaicin. It is found naturally in the latex of Euphorbia plants. Capsaicin (CAP) is the main pungent component in hot pepper. Resiniferatoxin and capsaicin and their analogues are exogenous ligands for the transient receptor potential cation channel subfamily V, member 1 (TRPV-1) or formerly known Vanilloid receptor 1 (VR1). The only known endogenous ligand for this receptor is the proton. TRPV-1 receptors are found on the visceral sensory nerve fibers of the unmyelinated type (C-fiber) and the thinly myelinated type (A-fiber). TRPV-1 functions as a modulator of sensory nerve responses to various noxious stimuli. Prolonged exposure to capsaicin lead to the desensitization of the TRPV1 receptors and under certain situation, complete ablation of the nerves. Resiniferatoxin induces the desensitization effect and neuronal ablation more potently than capsaicin and with minimal initial activation of the TRPV-1 neuron. Resiniferatoxin, and a number of agonists based on the structures of capsaicin and resiniferatoxin have been reported as potential analgesics through desensitization/denervation of theses neurons.

Andrew & Bhandari postulated in 1993 that resiniferatoxin had central and peripheral anti-emetic properties. Resiniferatoxin given subcutaneously had blocked the Intra-gastric copper sulphate, whole body radiation and Loperamide induced emetic response in ferrets. They proposed that resiniferatoxin acted by depletion of a neurotransmitter (Substance P) in the nucleus tractus solitarius. Andrew et al in 2000 showed that subcutaneous resiniferatoxin had initial emetic followed by anti-emetic properties in Suncus murinus, the house musk shrew. It was proposed that resiniferatoxin causes emesis by releasing Substance P at a critical site in the emetic pathway probably the nucleus tractus solitarius, and the depletion of Substance P is responsible for the subsequent anti-emetic effects. Another mechanisms that may also be involved is the desensitization of $NK_1$-receptors by internalization of $NK_1$-receptors Yamakuni et. al. in 2002 showed that subcutaneous resiniferatoxin in ferrets and dogs inhibited acute and delayed cisplatin and apomorphine induced emesis.

The prior art is deficient in the knowledge of the effect of local desensitization of the vagal afferents in controlling emesis as well as the anti-emetic properties for resiniferatoxin that can be achieved with local intra-gastric administration. The present invention fulfills this long standing need and desire in the art.

SUMMARY OF THE INVENTION

The present invention is directed to a method of alleviating acute or chronic nausea, vomiting or combination thereof in an individual consisting of localized ablation of vagal afferent nerves in the stomach or other regions of the gastrointestinal tract.

The present invention is also directed to a method of treating obesity in an individual in need of such treatment consisting of localized ablation of vagal afferent nerves in the stomach or other regions of the gastrointestinal tract.

The present invention is still further directed to a method of reducing insulin resistance in an individual in need of such treatment consisting of localized ablation of vagal afferent nerves in the stomach or other regions of the gastrointestinal tract

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1 shows inhibition of the emetic response following treatment with resiniferatoxin in dogs. Nausea and vomiting was induced using either balloon distention or intra-venous infusion of vasopressin (0.5 U/Kg infused over 20 minutes). Untreated represents control or baseline mean score of the emetic response was 26.3±4.0 and 29.0±6.2 for balloon distention and vasopressin stimuli respectively. Following, Resiniferatoxin infusion (250 ml of a 100 nM solution): the mean score with balloon distention was 11.7±4.2 (p=0.01) while the mean score with vasopressin was 16.3±5 (p=0.05).

DETAILED DESCRIPTION OF THE INVENTION

In one embodiment of the present invention there is provided a method of alleviating acute or chronic nausea, vomiting or combination thereof in an individual consisting of localized ablation of vagal afferent nerves in the stomach or other regions of the gastrointestinal tract. Specifically, the localized ablation of vagal afferent nerves is achieved by desensitization of the transient receptor potential vanilloid 1 expressed on the vagal afferent nerves. Moreover, the desensitization of the transient receptor potential vanilloid 1 is achieved by local administration of pharmacologically effective amount of resiniferatoxin or its derivatives. Particularly, the local administration of resiniferatoxin or derivatives is by endoscopic spraying onto the gastric mucosa. Specifically, the endoscopic spraying utilizes an endoscope with a glass or silicone treated spray catheter. Such local administration of resiniferatoxin or derivatives does not induce tachycardia, hypothermia or respiratory difficulties. The nausea or vomiting in the individual is due to gastrointestinal disorders, gastroparesis, antibiotics, non-steroidal anti-inflammatory agents, metabolic acidosis, administration of an anticancer agent or treatment. Specifically, the anticancer agent or treatment is selected from the group consisting of chemotherapy or radiotherapy.

In another embodiment of the present invention there is provided a method of treating obesity in an individual in need of such treatment consisting of localized ablation of vagal afferent nerves in the stomach or other regions of the gastrointestinal tract. Specifically, the localized ablation of vagal afferent nerves is achieved by desensitization of the transient receptor potential vanilloid 1 expressed on the vagal afferent nerves. Moreover, the desensitization of the transient receptor potential vanilloid 1 is achieved by local administration of pharmacologically effective amount of resiniferatoxin or its derivatives. The local administration of resiniferatoxin or derivatives is by endoscopic spraying onto the gastric mucosa. Specifically, the endoscopic spraying utilizes an endoscope with a glass or silicone treated spray catheter. In addition, the other regions of the gastrointestinal tract are the stomach, small bowel, visceral fat or peri-portal vein or a combination thereof. Also, the local administration of resiniferatoxin or derivatives does not induce tachycardia, hypothermia or respiratory difficulties. Specifically, the treatment heighten a sensation of satiety in the individual.

In yet another embodiment of the present invention there is provided a method of reducing insulin resistance in an individual in need of such treatment consisting of localized ablation of vagal afferent nerves in the stomach or other regions of the gastrointestinal tract. Specifically, the localized ablation of vagal afferent nerves is achieved by desensitization of the transient receptor potential vanilloid 1 expressed on the vagal afferent nerves. In addition, the desensitization of the transient receptor potential vanilloid 1 is achieved by local administration of a pharmacologically effective amount of resiniferatoxin or its derivatives. Particularly, the local administration of resiniferatoxin or derivatives is by endoscopic spraying onto the gastric mucosa. The endoscopic spraying utilizes an endoscope with a glass or silicone treated spray catheter. In addition, the other regions of the gastrointestinal tract are the stomach, small bowel, visceral fat or peri-portal vein or a combination thereof.

Moreover, the local administration of resiniferatoxin or derivatives does not induce tachycardia, hypothermia or respiratory difficulties. Specifically, the individual may have pre-diabetes, diabetes hypertension, dyslipidemia or cardiovascular disease.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Four dogs with surgically created jejunocutaneous fistulae 20 cm distal to the pylorus were used in this study. Nausea and vomiting were induced using two different stimuli, both of which are vagally dependent, at least in part: (1) Balloon inflation in the jejunum (2) Intravenous vasopressin infusion (0.5 U/Kg infused over 20 minutes). Nausea was assessed using a previously validated behavioral scoring system in addition to counting actual episodes of vomiting. After baseline observations, resiniferatoxin (250 ml of a 100 nM solution) was administered endoscopically using a spray catheter to coat the mucosal lining of the stomach under general anesthesia into the stomach. One week later, the response to balloon distention and vasopressin infusion was recorded again.

EXAMPLE 2

Resiniferatoxin infusion resulted in marked attenuation of nausea and vomiting to both stimuli: the mean score with balloon distention decreased from 26.3±4.0 to 11.7±4.2

(p=0.01) while the mean score with vasopressin decreased from 29.0±6.2 to 16.3±5 (p=0.05). Dogs appeared healthy although minor weight loss was observed. Thus, the present invention demonstrates that TRPV1-dependent pathways play a major role in the pathogenesis of nausea and vomiting and topically applied resiniferatoxin may be potentially beneficial in patients with intractable nausea in conditions such as gastroparesis.

The following references were cited herein.
1. Cheng F H, et al. *Eur J Pharmacol.* Jan. 31, 2005; 508(1-3):231-238.
2. Smith J E, et al. *Exp Physiol.* September 2002; 87(5):563-574.
3. Yamakuni H et al, *Eur J Pharmacol.* May 10, 2002; 442(3):273-278.
4. Rudd J A et al, *Eur J. Pharmacol.* Jun. 22, 2001; 422(1-3):185-195.
5. Andrews P et al, *Brain Res Dev Brain Res.* May 11, 2000; 121(1):29-34.
6. Hale J J, et al. *J Med Chem.* Nov. 5, 1998; 41(23):4607-4614.
7. Andrews P et al, *Eur J. Pharmacol.* Jul. 4, 1996; 307(3):305-313.
8. Tattersall F D et al, *Neuropharmacology.* 1996; 35(8):1121-1129.
9. Andrews P L et al, *Neuropharmacology.* August 1993; 32(8):799-806.
10. Shiroshita Y et al, *Eur J Pharmacol.* Nov. 27, 1997; 339(2-3):183-192.

Any patents or publications mentioned in this specification are indicative of the level of those skilled in the art to which the invention pertains. Further, these patents and publications are incorporated by reference herein to the same extent as if each individual publication was specifically and individually incorporated by reference.

One skilled in the art would appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method of alleviating acute or chronic nausea, vomiting or combination thereof in an individual comprising:
endoscopically spraying an effective amount of resiniferatoxin onto the gastric mucosa.

2. The method of claim 1, wherein said nausea or vomiting in the individual is due to gastrointestinal disorders, gastroparesis, antibiotics, NSAIDs, metabolic acidosis, or administration of an anticancer agent or treatment.

3. The method of claim 2, wherein the anticancer agent or treatment is chemotherapy or radiotherapy.

* * * * *